United States Patent [19]

Ungemach et al.

[11] Patent Number: 5,124,457
[45] Date of Patent: Jun. 23, 1992

[54] PHENCYCLIDINE AND PHENCYCLIDINE METABOLITES ASSAY, TRACERS, IMMUNOGENS AND ANTIBODIES

[75] Inventors: Frank S. Ungemach, Lake Villa; Daniel S. Nam, Chicago, both of Ill.

[73] Assignee: Abbott Laboratories, Abbott Park, Ill.

[21] Appl. No.: 563,882

[22] Filed: Aug. 6, 1990

Related U.S. Application Data

[63] Continuation of Ser. No. 866,193, May 21, 1986, abandoned.

[51] Int. Cl.$^5$ .................. C07D 405/12; C07D 405/06
[52] U.S. Cl. ..................................... 546/196; 544/375
[58] Field of Search ........................ 546/196; 544/375

[56] References Cited

U.S. PATENT DOCUMENTS

| | | | |
|---|---|---|---|
| 4,196,185 | 4/1980 | Focella et al. | 424/1 |
| 4,255,329 | 3/1981 | Ullman | 260/239 D |
| 4,281,065 | 7/1981 | Lin et al. | 435/188 |
| 4,351,760 | 9/1982 | Khanna et al. | 260/112 R |
| 4,420,568 | 12/1983 | Wang et al. | 436/536 |
| 4,446,065 | 5/1984 | Lin et al. | 260/112 R |
| 4,476,228 | 10/1984 | Huckzermeier et al. | 436/500 |
| 4,476,229 | 10/1984 | Fino et al. | 436/500 |
| 4,481,136 | 11/1984 | Khanna et al. | 260/112 R |
| 4,492,762 | 1/1985 | Wang et al. | 436/536 |
| 4,510,251 | 4/1985 | Kirkemo et al. | 436/536 |
| 4,585,862 | 4/1986 | Wang et al. | 544/319 |
| 4,588,697 | 5/1986 | Khanna et al. | 436/518 |
| 4,593,089 | 6/1986 | Wang et al. | 536/13.6 |
| 4,681,859 | 7/1987 | Kramer | 436/501 |

FOREIGN PATENT DOCUMENTS 2111476A 7/1983 United Kingdom ............ 436/546

OTHER PUBLICATIONS

Shipchandler, M. T., et al., "4'-[Aminomethyl]fluorescein and its N-Alkyl Derivatives: Useful Reagents in Immunodiagnostic Techniques". Analytical Biochemistry, 162:89–101 (1987).

Miceli, Joseph N., et al., "An Improved Method for the Quantitation of Phencyclide (PCP) in Biological Samples Utilizing Nitrogen-Detection Gas Chromatography", Journal of Analytical Toxicology, 5:29–32, Jan.-/Feb., 1981.

Lewellen, Larry J., et al., "Nitrogen-Sensitive Gas Chromatographic Detection and Quantitation of Nanogram Levels of Phencyclidine in Whole Blood", Journal of Analytical Toxicology, 72–75, Mar./Apr., 1979.

Egen, N. B. et al., "Isolation of Monoclonal Antibodies to Phencyclidine from Ascites Fluid by Preparative Isoelectric Focusing in the Rotofor," Anal. Biochemistry 172, 488–494 (1988).

Tillotson, J. A., et al., "Fluorometric Apoprotein Titration of Urinary Riboflavin," Anal. Biol. Chemistry 107,214–219 (1980).

Rhodes, M. B., et al., "The Flavoprotein-Apoprotein System of Egg White," J. Biol. Chemistry 234, No. 8, 2054–2060 (1959).

Nishikimi et al., "Flavin-Protein Interaction in Egg White Flavoprotein," J. Biochem. 73, 1233–1242 (1973).

Murthy, U. S., et al., "The Interaction of Riboflavin with a Protein Isolated from Hen's Egg White: A Spectrofluorimetric Study." Biochimica et Biophysica Acta, 434, 69–81 (1976).

Heveran, J. E., "Determination of Phencyclidine by Radioimmunoassay," J. Forensic Sciences, vol. 25, No. 1, pp. 79–87 (1980).

Primary Examiner—John M. Ford
Attorney, Agent, or Firm—Thomas M. Breininger

[57] ABSTRACT

The present invention is directed to a fluorescence polarization assay for phencyclidine and phencyclidine derivatives, to the various components needed for preparing and carrying out such an assay, and to methods of making these components. Specifically, tracers, immunogens and antibodies are disclosed, as well as methods for making them. The tracers and the immunogens are made from substituted phencyclidine compounds. A fluorescein moiety is included in the tracer, while a poly(amino acid) forms a part of the immunogen. The assay is conducted by measuring the degree of polarization retention of plane polarized light that has been passed through a sample containing antiserum and tracer.

5 Claims, 5 Drawing Sheets

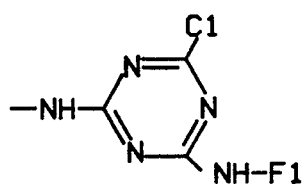
FIG. 11-1
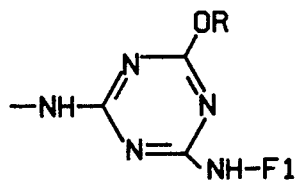
FIG. 11-2
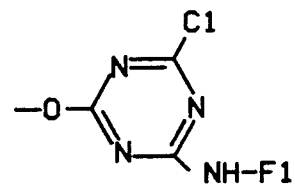
FIG. 11-3
−NH−CO−F1
FIG. 11-4
−CO−NH−F1
FIG. 11-5
−CNH−NH−F1
FIG. 11-6
−NH−CO−NH−F1
FIG. 11-7
−NH−CS−NH−F1
FIG. 11-8
−O−CO−NH−F1
FIG. 11-9
−O−CS−NH−F1
FIG. 11-10

EXAMPLE XIII

EXAMPLE XIV

EXAMPLE XVI

EXAMPLE XV

EXAMPLE X

EXAMPLE VI

EXAMPLE IX

EXAMPLE XII

PHENCYCLIDINE AND PHENCYCLIDINE METABOLITES ASSAY, TRACERS, IMMUNOGENS AND ANTIBODIES

This application is a continuation of application Ser. No. 06/866,193, filed May 21, 1986, now abandoned.

BACKGROUND OF THE INVENTION

1. Technical Field

The present invention relates to a method and reagents for performing a fluorescence polarization immunoassay (FPIA) to determine the presence or amount of phencyclidine and phencyclidine metabolites in fluids, especially biological fluids such as urine, serum or plasma, and to a method of making the reagents. The invention relates particularly to (1) reagents (tracers and antibodies) for determining the presence or amount of phencyclidine and phencyclidine metabolites in a sample; (2) immunogen compounds used to raise antibodies; (3) synthetic methods (for making tracer and immunogen compounds); and (4) analytical methods for conducting the assay.

2. Background Art

Phencyclidine is a synthetic drug with potent analgesic and anesthetic properties. The drug has been shown to produce serious and prolonged post-anesthetic confusion and delirium. Its tendency to produce hallucinations, euphoria, distortions in perceptions, and feelings of dissociation have lead to illicit use and abuse. Recurring abuse has intensified efforts to prevent its manufacture and distribution. Consistent with these efforts, there exists a need for detection methods that are rapid, reliable and selective for phencyclidine and phencyclidine metabolites.

Phencyclidine is metabolized into two major metabolites, 4-phenyl-4-piperidinocyclohexanol and 1-(1-phenylcyclohexyl)-4-hydroxypiperidine, which are excreted mostly in the urine along with the corresponding glucuronide conjugates. Detection of either phencyclidine or phencyclidine metabolites indicates phencyclidine use.

The biological fluid most frequently tested is urine. Urine samples are non-invasive of the body, and are generally more accessible than blood samples. Although testing of other biological fluids is a possibility, they have not been extensively investigated with respect to such assays.

In the past, urine samples have been tested for the presence of phencyclidine and phencyclidine metabolites by thin layer chromatography (TLC), enzyme immunoassay (EIA), gas chromatography (GC) or high performance liquid chromatography (HPLC) assays. These methods are not without drawbacks; e.g., the assay time involved in these methods is typically lengthy.

In assays for other substances, competitive binding immunoassays have provided a more satisfactory alternative. Typically, competitive binding immunoassays are used for measuring ligands in a test sample. (For purposes of this disclosure, a "ligand" is a substance of biological interest to be quantitatively determined by a competitive binding immunoassay technique). The ligands compete with a labeled reagent (a "ligand analog" or "tracer") for a limited number of receptor binding sites on antibodies specific to the ligand and ligand analog. The concentration of ligand in the sample determines the amount of ligand analog which binds to the antibody; the amount of ligand analog that will bind is inversely proportional to the concentration of ligand in the sample, because the ligand and the ligand analog each bind to the antibody in proportion to their respective concentrations.

FPIA techniques provide a quantitative means for measuring the amount of tracer-antibody conjugate produced in a competitive binding immunoassay. Such procedures are based on the principle that a fluorescent labeled compound, when excited by plane polarized light, will emit fluorescence having a degree of polarization inversely related to its rate of rotation. Accordingly, when a tracer-antibody conjugate having a fluorescent label is excited with plane polarized light, the emitted light remains highly polarized because the fluorophore is constrained from rotating between the time that light is absorbed and emitted. In contrast, when an unbound tracer is excited by plane polarized light, its rotation is much faster than the corresponding tracer-antibody conjugate and the molecules are more randomly oriented. As a result, the light emitted from the unbound tracer molecules is depolarized.

A problem that heretofore has prevented the accurate determination of phencyclidine and other "drugs of abuse" in urine by FPIA techniques is that of riboflavin interference. Riboflavin, or vitamin $B_2$, is a common constituent of many foods and of commercially available vitamin supplements. Riboflavin is excreted primarily in the urine and has a fluorescence spectrum quite similar to that of fluorescein. As a result, the presence of riboflavin in even moderate amounts in urine samples creates an interference which can produce erroneous data. While ordinary consumption of riboflavin is unlikely to produce more than trace amounts of riboflavin in the urine, test results can readily be distorted by the consumption of excessive quantities of vitamin supplements by persons wishing to prevent detection of phencyclidine.

The present invention offers an advance in the art in that highly sensitive tracers, a method for making the tracers, and an assay using the tracers are provided specifically for the determination of phencyclidines and phencyclidine metabolites without riboflavin interference.

SUMMARY OF THE INVENTION

The present invention is directed to a fluorescence polarization assay for phencyclidine and phencyclidine metabolites; to tracers, immunogens and antibodies for use in the assay; and to methods for making the tracers, immunogens and antibodies.

A first aspect of the invention relates to the discovery of unique tracers and immunogens having novel structures. According to the first aspect of the invention, the tracers and the immunogens can both be represented by the structural formula shown in FIG. 5 where:

W is CH or N;

R is a linking group including up to 4 heteroatoms and having a total of from 0 to 8 carbon atoms and heteroatoms;

Z is NH, CO or CNH;

n is 0 or 1 when W is N and n is 1 when W is CH; and

Q is a poly(amino acid), a poly(amino acid) derivative, fluorescein or a fluorescein derivative.

When Q is a poly(amino acid) or a derivative thereof, the compound can be used as an immunogen. When Q is fluorescein or a derivative thereof, the compound can be used as a tracer.

A second aspect of the invention relates to antibodies raised by the novel immunogens of the invention. According to the second aspect of the invention, antibodies are prepared in response to a compound according to the aforementioned structural formula (FIG. 5), when Q is poly(amino acid) or a derivative thereof.

According to a third aspect of the invention, an immunogen is made by a method comprising the step of coupling a compound represented by the structural formula shown in FIG. 2, where:

W is CH or N;

R is a linking group including up to 4 heteroatoms and having a total of from 0 to 8 carbon atoms and heteroatoms when Z is NH, CN or OH and having a total of from 1 to 8 carbon atoms when Z is COOH or CHO;

Z is $NH_2$, COOH, CN, CHO or OH; and n is 1 when W is CH and n is 0 or 1 when W is N; with a poly(amino acid) or a derivative of a poly(amino acid).

According to a fourth aspect of the invention, a method is provided for making a tracer by coupling a compound represented by the structural formula shown in FIG. 3, where:

W is CH or N;

R is a linking group including up to 4 heteroatoms and having a total of from 0 to 8 carbon atoms and heteroatoms when Z is NH, CN or OH and having a total of from 1 to 8 carbon atoms when Z is COOH or CHO;

Z is $NH_2$, COOH, CN, CHO or OH; and n is 1 when W is CH and n is 0 or 1 when W is N; with fluorescein or a derivative of fluorescein.

A fifth aspect of the invention relates to the elimination of potential fluorescence interference by riboflavin. Riboflavin binding protein (RBP) is added either directly to each sample or to one or more of the reagents utilized in the assay, wherein it binds all riboflavin present into RBP-riboflavin complexes, thus eliminating fluorescence interference.

According to a sixth aspect of the invention, a process for detecting or measuring the concentration of phencyclidine and phencyclidine metabolites is provided. A sample is contacted with phencyclidine derivative antiserum, and a fluorescein-containing phencyclidine derivative capable of producing a detectable fluorescence polarization response to the presence of the phencyclidine derivative antiserum. Plane polarized light is then passed through the solution to obtain a fluorescence polarization response, and this response is detected as a measure of the amount of phencyclidine and phencyclidine metabolite in the sample.

Further objects and attendant advantages of the invention will be best understood from a reading of the following detailed description taken together with the Examples and appended drawings.

BRIEF DESCRIPTION OF THE DRAWINGS

In the drawing Figures hereof the symbol "Fl" represents fluorescein or a fluorescein derivative and the various other symbols are noted in the Detailed Description, infra.

FIG. 11 shows various linkages that couple the fluorescein moiety to the precursor at the Z position in FIG. 10, when FIG. 10 represents a precursor for the tracers shown in FIGS. 7 and 9.

DETAILED DESCRIPTION OF THE PREFERRED EMBODIMENTS

The various aspects of the invention will now be discussed in relation to the Figures and/or the Examples.

The present invention involves the use of fluorescein and derivatives of fluorescein. In particular, a necessary property of fluorescein and its derivatives for the usefulness of the tracer compounds of the present invention is the fluorescence of fluorescein. Fluorescein exists in two tautomeric forms, illustrated in FIG. 4, depending on the acid concentration (pH) of the environment. In the open (acid form), there are a number of conjugated double bonds which make that form of fluorescein (and compounds containing a fluorescein moiety) capable of absorbing blue light and emitting green fluorescence after an excited state lifetime of about 4 nanoseconds. When the open and closed forms coexist, the relative concentration of molecules in the open and closed forms is easily altered by adjustment of the pH level. Generally, the tracer compounds of the present invention exist in solution as biologically acceptable salts such as sodium, potassium, ammonium and the like, which allows the compounds to exist in the open, fluorescent form, when employed in the analytical methods of the present invention. The specific salt present will depend on the buffer employed to adjust the pH level. For example, in the presence of a sodium phosphate buffer, the compounds of the present invention will generally exist in the open form, as a sodium salt.

As used herein, the term "fluorescein," either as an individual compound or as a component of a larger compound, is meant to include both the open and closed forms, if they exist for a particular molecule, except in the context of fluorescence. An open form is necessary for the fluorescence to occur.

Figure 4:
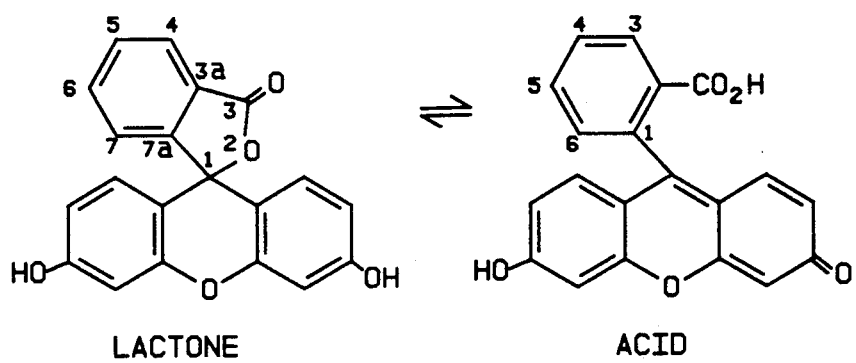
FIG. 4 shows the alternate structural formula and names of the fluorescein moiety included in the tracers of the present invention.

The numbering of carbon atoms of the fluorescein molecule varies, depending upon whether the open or closed form of the molecule is considered. Accordingly, the literature concerning fluorescein and its compounds is not uniform as to carbon atom numbering. In the closed form, the para-carbon to the carbonyl of the lactone on the phenyl ring is numbered 6 (this is sometimes denominated "isomer II"). In the open form, the para-carbon to the carboxylic acid group on the phenyl ring is numbered 5 (this is sometimes denominated "isomer I"). FIG. 4 illustrates these isomers. For the purpose of this disclosure the numbering of the closed form is adopted because the raw materials used in the syntheses are most popularly numbered with that system. The carbon atom of fluorescein and its compounds which is opposite the carboxyl group is therefore numbered "6" for the purposes of the present disclosure.

A tracer which is not complexed to an antibody is free to rotate in less than the time required for absorption and re-emission of fluorescent light. As a result, the re-emitted light is relatively randomly oriented so that the fluorescence polarization of a tracer not complexed to an antibody is low, approaching zero. Upon complexing with a specific antibody, the tracer-antibody complex thus formed assumes the rotation of the antibody molecule which is slower than that of the relatively small tracer molecule, thereby increasing the polarization observed. Therefore, when a ligand competes with the tracer for antibody sites, the observed polarization of fluorescence of the tracer-antibody complex becomes a value somewhere between that of the tracer and tracer-antibody complex. If a sample contains a high concentration of the ligand, the observed polarization value is closer to that of the free tracer, i.e., low. If the test sample contains a low concentration of the ligand, the polarization value is closer to that of the bound tracer, i.e., high. By sequentially exciting the reaction mixture of an immunoassay with vertically and then horizontally polarized light and and analyzing only the vertical component of the emitted light, the polarization of fluorescence in the reaction mixture may be accurately determined. The precise relationship between polarization and concentration of the ligand to be determined is established by measuring the polarization values of calibrators with known concentrations. The concentration of the ligand can be extrapolated from a standard curve prepared in this manner.

The particular tracers formed in accordance with this invention have been found to produce surprisingly good assays, as will be demonstrated later in this disclosure.

THE REAGENTS

Figure 5:
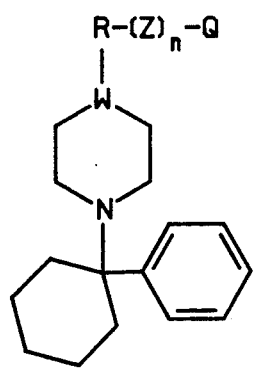
FIG. 5 shows a general structural formula for the tracers and the immunogens of the present invention.

Both the immunogens and the tracers of the present invention can be represented by the general structural formula set forth in the Summary of the Invention, and illustrated in FIG. 5. When Q is a poly(amino acid), the structure represents the immunogen; when Q is a fluorescein derivative, the structure represents the tracer.

The objective is to have competition between phencyclidine and phencyclidine metabolites and the tracer for the recognition sites of the antibody. Great variations in the structure of the haptens and tracers are allowed in achieving this goal. For the purposes of this invention, "haptens" are precursors of the immunogens, comprising generally a substituted phencyclidine derivative and a linking group to the poly(amino acid) carrier.

THE STRUCTURE OF THE IMMUNOGENS

Usable antibodies can be produced from a variety of phencyclidine derivatives. Such antibodies are useful in phencyclidine and phencyclidine metabolites assay according to the invention when combined with the appropriate tracer.

Figure 6:
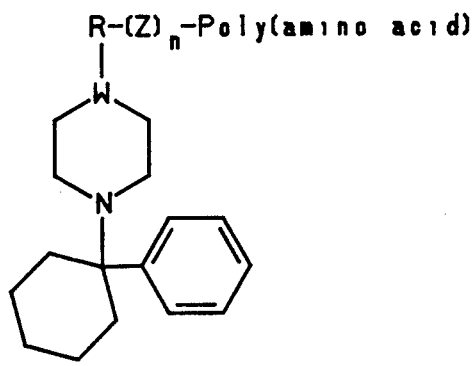
FIG. 6 shows a general structural formula for the immunogens of the present invention.
Figure 8:
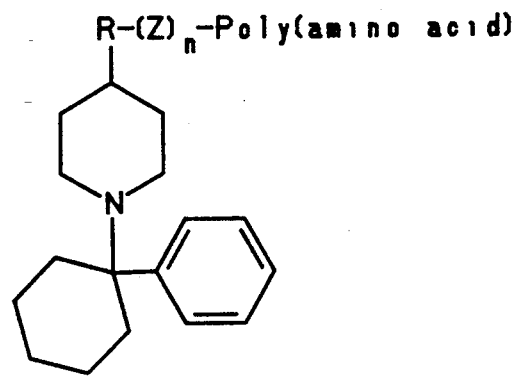
FIG. 8 shows a structural formula for preferred immunogens of the present invention.

The immunogens of the present invention have the general structural formula shown in FIG. 6, and in the preferred form of the invention, the immunogens have the structural formula shown in FIG. 8. This structure is preferred because the best recognition of the common moiety of phencyclidine and phencyclidine metabolites, the phenyl ring, occurs when the piperidine ring is substituted at a position as distant as possible from the phenyl ring. Although bovine serum albumin is the poly(amino acid) in this preferred form, it should be understood that various protein carriers may be employed, including albumins, serum proteins, e.g., globulins, ocular lens proteins, lipoproteins and the like. Illustrative protein carriers include, in addition to bovine serum albumin, keyhole limpet hemocyanin, egg ovalbumin, bovine gamma-globulin, thyroxine binding globulin, etc. Alternatively, synthetic poly(amino acids) may be prepared having a sufficient number of available amino groups such as lysines. The corresponding glutaraldehyde derivative of the above poly(amino acid) carriers may also be employed when the hapten coupling group is an amino group.

The immunogens can be prepared by coupling a compound of the class shown in FIG. 2 with a poly(amino acid) or a derivative of a poly(amino acid), as will be discussed in the context of the synthetic method and the Examples below.

THE STRUCTURE OF THE TRACERS

Figure 7:
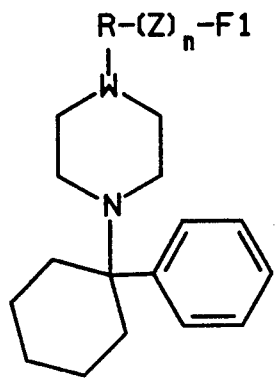
FIG. 7 shows a general structural formula for the tracers of the present invention.
Figure 9:
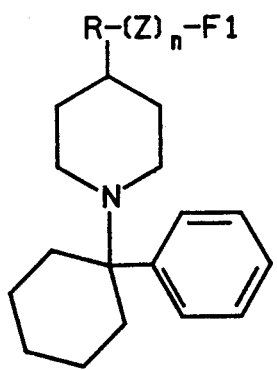
FIG. 9 shows a structural formula for preferred tracers of the present invention.

The possible variations in the structure of the tracers of the invention are even greater than the possible variations in the structure of the haptens thereof. The tracers of the present invention have the general structural formula shown in FIG. 7, where Fl represents a fluorescein moiety or a fluorescein derivative. In a preferred form of the invention, the tracers have the structural formula shown in FIG. 9.

The tracer is a phencyclidine derivative that is linked to a fluorescein derivative by, e.g., an amido, amidino, triazinylamino, carbamido, thiocarbamido, carbamoyl, thiocarbamoyl, or sulfomylcarbamoyl group, as shown in FIG. 11. The tracers are prepared by linking the appropriate fluorescein derivative to a phencyclidine derivative containing an amino, carboxylic acid, hydroxy, imidate, hydrazide, chloroformate, chlorothioformate, chlorosulfonyl-carbamoyl, isocyanate, thioisocyanate, or similar group, as will be discussed in the context of the synthetic method and the Examples below.

By way of example, any of the following fluorescein derivatives can be used:

 Fl—NH$_2$  fluorescein amine

 Fl—CO$_2$H  carboxyfluorescein

 Fl—NHCOCH$_2$I  α-iodoacetamidofluorescein

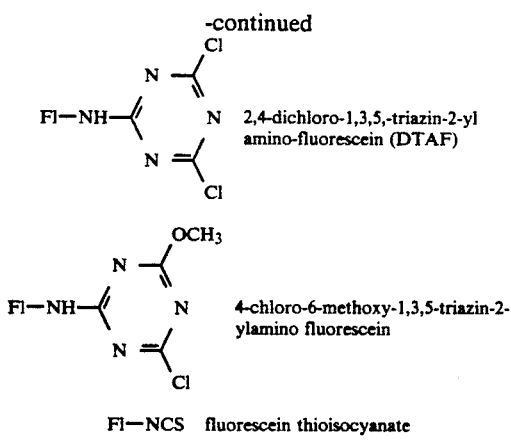

Fl—NH—[2,4-dichloro-1,3,5,-triazin-2-yl structure] 2,4-dichloro-1,3,5,-triazin-2-yl amino-fluorescein (DTAF)

Fl—NH—[4-chloro-6-methoxy-1,3,5-triazin-2-yl structure] 4-chloro-6-methoxy-1,3,5-triazin-2-ylamino fluorescein Fl—NCS    fluorescein thioisocyanate

THE ANTIBODIES

The antibodies of the present invention are prepared by developing a response in animals to the immunogens described above. The immunogen is administered to animals such as rabbits or sheep by a series of injections, in a manner well-known to those skilled in the art.

SYNTHETIC METHODS

Figure 10:
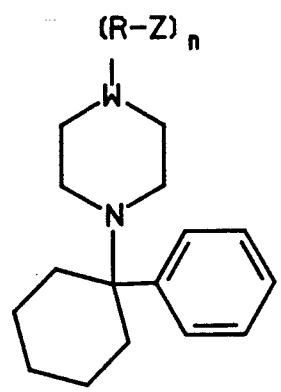
FIG. 10 shows a precursor for the immunogens shown in FIGS. 6 and 8 and for the tracers shown in FIGS. 7 and 9.

Both the immunogens and the tracers of the present invention can be made from a precursor having the general structural formula shown in FIG. 10, where:
W is CH or N;
R is a linking group including up to 4 heteroatoms and having a total of from 0 to 8 carbon atoms and heteroatoms when Z is $NH_2$, CN or OH and having a total of from 1 to 8 carbon atoms and heteroatoms when Z is COOH or CHO;
Z is $NH_2$, COOH, CN, CHO, or OH when the preparation is directed to an immunogen, and Z is $NH_2$, COOH, CN or OH when the preparation is directed to a tracer; and
n is 1 when W is CH and n is 0 or 1 when W is N.

THE SYNTHESIS OF THE IMMUNOGENS

Figure 2:
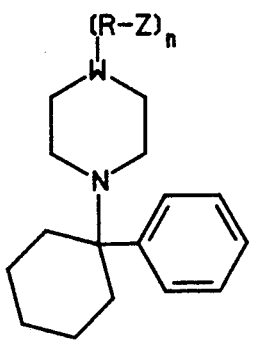
FIG. 2 shows a class of reactants for a method of making an immunogen in accordance with the present invention.
Figure 3:
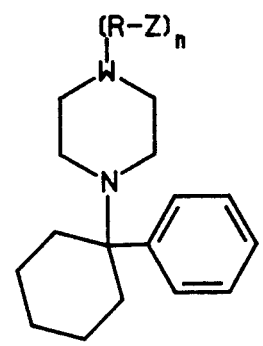
FIG. 3 shows a class of reactants for a method of making a tracer in accordance with the present invention.
Figure 18:
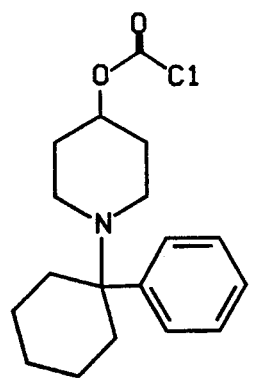

The immunogens of the present invention are made by coupling a hapten, such as that shown by the general structure of FIG. 2 when Z is $NH_2$, COOH, CN, CHO, or OH, to a poly(amino acid). The poly(amino acid) moiety can be linked to the hapten by an amide, an amidine, an alkyl, a urea, a thiourea, a carbamate, or a thiocarbamate linkage. In a preferred embodiment, the poly(amino acid) is bovine serum albumin (BSA) and the hapten is shown in FIG. 18. The hapten is preferably coupled under conditions normally used to form carbamate linkages, which conditions are well known to those skilled in the art. It is most preferred that pH conditions approximating pH 8.0 be used for forming the desired carbamate linkages, as these are the most effective for forming these linkages in this context.

The immunogens are prepared by coupling a hapten containing an —$NH_2$, —$CO_2H$, —$CONHNH_2$, —CNOR, —CHO, —NCO, —NCS, —OCOCl or —OCSCl group to a poly(amino acid). The —$NH_2$ case can be coupled by activating the carboxylic acid group on the poly(amino acid) in the presence of the —$NH_2$ group. The activation of the carboxylic acid groups on the poly(amino acid) can be accomplished by mixing the hapten and the poly(amino acid) with 1-ethyl-3-(3-dimethylaminopropyl)carbodiimide (EDC), N,N'-dicyclohexylcarbodiimide (DCC), 1-cyclohexyl-3-(2-morpholinoethyl)carbodiimide metho-p-toluenesulfonate, or the like. The —$CO_2H$ case is also coupled by the activation method (EDC) or the active ester method. The —$CONHNH_2$ case is coupled in the same manner as for the non-aromatic amino case. The —CNOR case which is prepared from the corresponding cyano compound, is coupled directly to the poly(amino acid). The —CHO case is coupled to the poly(amino acid) by reductive amination. The poly(amino acid) is mixed with the —CHO hapten and the resulting imine is reduced with sodium cyanoborohydride to yield alkylated amines on the poly(amino acid). The isocyanate (—NCO) and isothiocyanate (—NSC) cases, which are prepared from the corresponding amino compound and chloroformate (—OCOCl) and chlorothioformate (—OCSCl) cases which are prepared from the corresponding alcohol compound, produce urea, thiourea, carbamate and thiocarbamate linkages, respectively. This is accomplished by direct coupling of the hapten to the poly(amino acid).

The synthesis of the above haptens (immunogen precursors) are accomplished in very similar ways. FIG. 2 shows an immunogen precursor class in accordance with a preferred embodiment of the method of the present invention.

In general, the hapten is prepared by reaction of the appropriate piperidine derivative with cyclohexanone in the presence of cyanide. The coupled product is then reacted with phenyl magnesium bromide to yield the hapten precursor. The hapten precursor is then converted into the hapten.

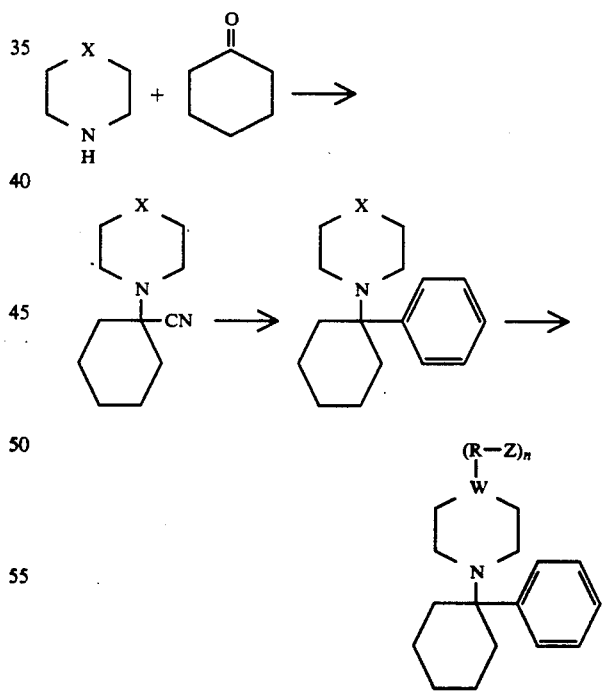

In the case where W is N, X is benzyl amine. The benzyl group is removed after formation of the phencyclidine derivative. This secondary amine is a suitable hapten. It is possible to alkylate the amine with an alkyl halide (Cl, Br or I), e.g., bromoacetonitrile, 3-bromopropanol, 4-bromobutyric acid or the like, to prepare suitable haptens. It is also possible to form the chloroformamide derivative, which could make a suitable hapten, or form an amide derivative with an active ester, e.g., succinic anhydride, cyanoacetyl chloride or the like, containing a suitable group useful for coupling to a carrier protein. In the case where W is CH, X is CHOH, after formation of the phencyclidine derivative, a large variety of haptens may be prepared. The alcohol may be alkylated with an alkyl halide (Cl, Br, or I), containing a suitable group useful for coupling to a carrier protein, by standard procedures to form ether derivatives. The alcohol may be converted into the corresponding halogen derivative, such as, bromo, chloro or iodo, which will react with carbanion, alcohol or amine derivatives of compounds containing a suitable group for coupling to a carrier protein. The alcohol can be oxidized to the corresponding ketone which may be derivatized by known methods to a variety of compounds containing a suitable group useful for coupling to a carrier protein, e.g., Wittig reagents, alkoxyamine compounds, reductive amination with amino compounds or the like. Reductive amination of the ketone with ammonium acetate results in the amino derivative where X is $CHNH_2$. The amino compound is suitable as a hapten or may be derivatized by known methods to a variety of hapten compounds analogous to the case where W is N and n is 0.

Nitrile derivatives (Z=CN) are converted to alkoxy imidates (Z=CNOR) by treating the nitrile with anhydrous alcohol and hydrogen chloride gas. The hydrazide derivatives (Z=$CONHNH_2$) are prepared from the corresponding carboxylic acid derivatives by active ester coupling with hydrazine or by reacting hydrazine with the corresponding carboxylic ester derivative. Amines (Z=$NH_2$) are convertible to the isocyanate or thioisocyanate derivatives and alcohols (Z=OH) are convertible to chloroformate and chlorothioformate derivatives by reaction of the amine or the alcohol with phosgene or thiophosgene.

Aldehydes and ketones can be condensed with (aminohydroxy)alkylcarboxylic acids, such as $NH_2OCH_2CO_2H$, to produce substituted oxime derivatives. The oxime alkyl carboxylic acid derivatives can be partially reduced to the corresponding (aminohydroxy)alkylcarboxylic acid derivatives. The same type of condensation and reduction can be accomplished with hydrazine and hydrazine derivatives.

The Synthesis of the Tracers

Figure 13:
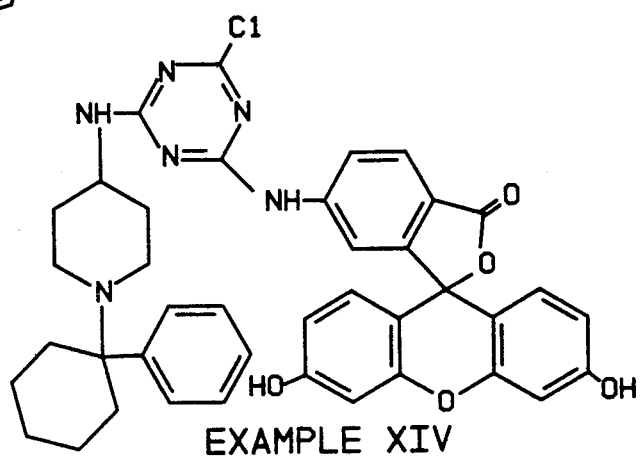

The tracers of the present invention are made by coupling a fluorescein moiety, or a derivative of fluorescein, to the general structure shown in FIG. 10 when Z is $NH_2$, COOH, CNOR or OH. The fluorescein moiety can be linked to the amino, carboxyl, imidate or alkoxy functional group by an amide, an amidine, a urea, a thiourea, a carbamate, a thiocarbonate, triazinylamino or sulfonylcarbamate linkage, as shown in FIG. 11. In the presently preferred embodiment, the fluorescein derivative is 6-((4,6-dichloro-1,3,5-triazin-2-yl)amino) fluorescein, and this is coupled to the precursor 4-amino-1-(1-phenylcyclohexyl)-piperidine in a co-solvent, e.g., methanol, dimethylsulfoxide, or the like, in the presence of a base, e.g., triethylamine or the like. The structure is shown in FIG. 13. Useable tracers can be prepared from a variety of phencyclidine derivatives.

All phencyclidine derivatives that have a terminal amino group, such as amino, hydrazinyl, hydrazido or the like, are coupled to carboxyfluorescein by the active ester method or the mixed anhydride method, and coupled to fluorescein isothiocyanate, DTAF or alkoxy DTAF by simply mixing the two materials in solution. The amino group can be converted to the isocyanate and thioisocyanate groups by reaction with phosgene and thiophosgene, respectively. These are then condensed with aminofluorescein to produce the tracer.

All phencyclidine derivatives that have a terminal carboxylic acid group, such as carboxylic acid, (aminohydroxy)alkylcarboxylic acid or the like, are coupled to aminofluorescein by the active ester method.

All phencyclidine derivatives that have a terminal hydroxy group can be coupled to fluorescein by reaction with DTAF, iodoacetamidofluorescein or fluorescein isothiocyanate in solution. The hydroxy group can be converted to the chlorosulfonylcarbamoyl, chloroformate and chlorothioformate groups by reaction with chlorosulfonylisocyanate, phosgene and thiophosgene, respectively. These derivatives are then coupled to aminofluorescein in solution to produce the tracer.

All phencyclidine derivatives that have a terminal nitrile group are converted to imidates in anhydrous alcohol in the presence of hydrogen chloride gas. The imidate is then coupled to fluorescein amine in solution to prepare the tracer.

The preparation of the various amino, carboxylic acid, hydroxy and nitrile derivatives of the anilide derivatives were described above in the immunogen preparation section.

THE ASSAY

Figure 1:
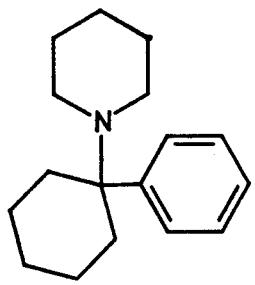
FIG. 1 shows the general structure of the class of phencyclidine to be quantitatively or qualitatively determined in accordance with the present invention.

The particular tracers and antibodies of the present invention have been found to produce surprisingly good results in fluorescence polarization assays for phencyclidine and phencyclidine metabolites. FIG. 1 shows the general structure of the phencyclidine and phencyclidine metabolites that can be quantitatively or qualitatively determined in accordance with the present invention. The assay of the present invention provides a more rapid phencyclidine and phencyclidine metabolite assay method than most prior art methods, because it requires no specimen treatment before analysis. The assay system accurately measures the presence or quantity of phencyclidine and phencyclidine metabolites in a sample, because antibody specificity precludes detection of compounds other than phencyclidine-like compounds.

In accordance with the analytical methods of the present invention; i.e., the methods of determining phencyclidine and phencyclidine metabolites by a fluorescence immunoassay procedure using the tracer compounds and immunogens of the invention, a sample containing or suspected of containing phencyclidine and phencyclidine metabolites is intermixed with a biologically acceptable salt of a tracer and an antibody specific to phencyclidine and phencyclidine metabolites and the tracer. The antibody is produced using the immunogen as described above. The phencyclidine and phencyclidine metabolites and tracer compete for limited antibody sites, resulting in the formation of complexes. By maintaining constant the concentration of tracer and antibody, the ratio of phencyclidine and phencyclidine metabolites-antibody complex to tracer-antibody complex that is formed is directly proportional to the amount of phencyclidine and phencyclidine metabolites in the sample. Therefore, upon exciting the mixture with linearly polarized light and measuring the polarization of the fluorescence emitted by a tracer and a tracer-antibody complex, one is able to quantitatively determine the amount or qualitatively determine the presence of phencyclidine and phencyclidine metabolites in the sample.

The results can be quantified in terms of net millipolarization units and span (in millipolarization units). The measurement of net millipolarization units indicates the maximum polarization when a maximum amount of the tracer is bound to the antibody, in the absence of any phencyclidine or phencyclidine metabolites. The higher the net millipolarization units, the better the binding of the tracer to the antibody. The span is an indication of the difference between the net millipolarization and the amount of tracer bound to the antibody at the minimum phencyclidine concentration above which the sample is defined as containing phencyclidine and/or phencyclidine metabolites. A larger span provides for a better numerical analysis of data. The preferred antibody-tracer combination has a span of at least 18 millipolarization units, but a span of at least 5 millipolarization units is acceptable. It is important to note that the span varies depending on the sample size used which in turn may alter the preferred combination.

Table I shows the results obtained with various embodiments of the present invention, in terms of span and net millipolarization units at a sample size of 2 μl. In all instances, bovine serum albumin was used as the protein carrier. As seen from the data in Table I, an assay produced from an immunogen made from the hapten of FIG. 18 used in combination with the tracer of FIG. 13 and a 2 μl sample size provides excellent results. Accordingly, this combination is presently the most preferred form of the invention for a sample size of 2 μl. In addition, the hapten/tracer combinations represented by the combinations of FIGS. 18 and 12, FIGS. 18 and 14, and FIGS. 18 and 15, and FIGS. 18 and 16 also produced acceptable results and are alternative preferred combinations.

TABLE I

Figure 12:
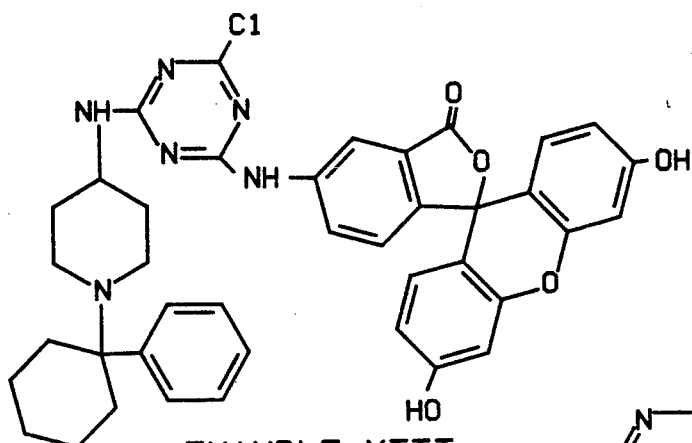
FIGS. 12 through 16 show various examples of structures of tracers in accordance with the present invention.
Figure 15:
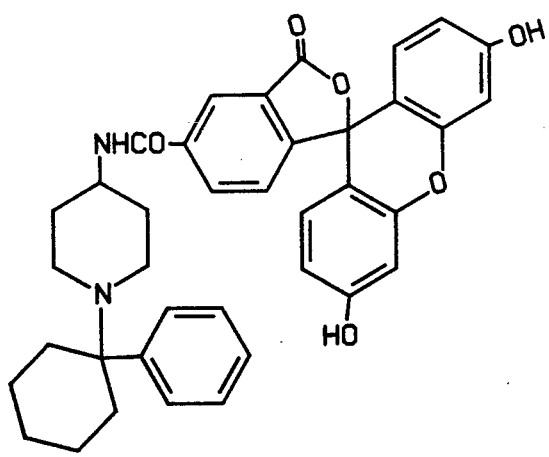
Figure 14:
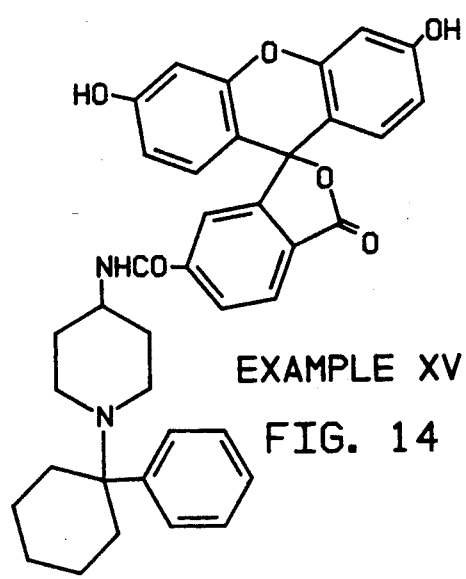
Figure 16:
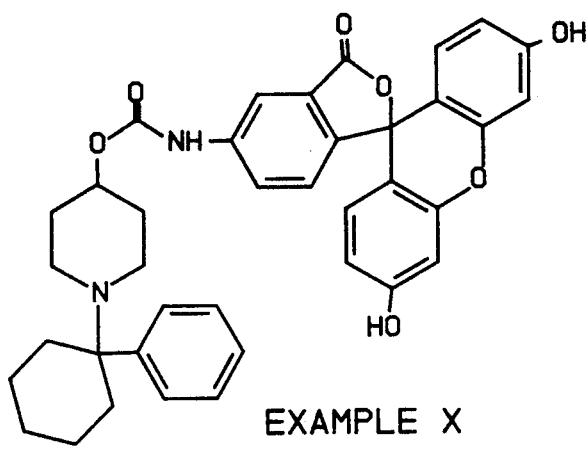
Figure 17:
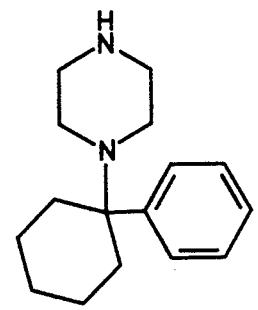
FIGS. 17 through 19 show various examples of structures of hapten reactants used to form the immunogens of the present invention.
Figure 19:
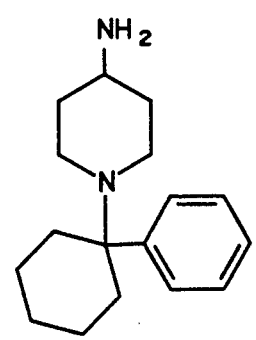

| Hapten used in Immunogen for Antibody | Tracer | Net Polarization* | Span** |
|---|---|---|---|
| FIG. 18 | FIG. 12 | 176 | 16 |
| FIG. 18 | FIG. 13 | 172 | 18 |
| FIG. 18 | FIG. 14 | 164 | 16 |
| FIG. 18 | FIG. 15 | 159 | 15 |
| FIG. 18 | FIG. 16 | 187 | 12 |
| FIG. 17 | FIG. 12 | 129 | 5 |
| FIG. 17 | FIG. 13 | 125 | 5 |
| FIG. 17 | FIG. 14 | 102 | 4 |
| FIG. 17 | FIG. 15 | 110 | 6 |
| FIG. 17 | FIG. 16 | 119 | 4 |
| FIG. 19 | FIG. 12 | 137 | 4 |
| FIG. 19 | FIG. 13 | 142 | 2 |
| FIG. 19 | FIG. 14 | 155 | 6 |
| FIG. 19 | FIG. 15 | 140 | 5 |
| FIG. 19 | FIG. 16 | 141 | 4 |

*In millipolarization units
**In millipolarization units at a phencyclidine concentration of 75 ng/ml and a 2 μl sample size.

The pH at which the method of the present invention is practiced must be sufficient to allow the fluorescein moiety of the tracers to exist in their open form. The pH may range from about 3 to 12, more usually in the range of from about 5 to 10, most preferably from about 6 to 9. Various buffers may be used to achieve and maintain the pH during the assay procedure. Representative buffers include borate, phosphate, carbonate, tris, barbital and the like. The particular buffer employed is not critical to the present invention, but the tris and phosphate buffers are preferred. The cation portion of the buffer will generally determine the cation portion of the tracer salt in solution.

Riboflavin binding protein (RBP) is added to the sample or to one or more of the assay reagents in order to bind any riboflavin present in the sample into RBP-riboflavin complexes, thus eliminating potential fluorescence interference. RPB is a protein of approximately 32,000 M.W. which is isolated from egg whites. Upon isolation from the egg, each molecule of RBP contains one molecule of riboflavin. This, the holoprotein form of RBP, must be converted to the apoprotein form by dialysis, under acidic conditions, to remove the bound riboflavin. The RBP apoprotein utilized in the present invention is commercially available from Sigma Chemical Company, St. Louis, Mo. The amount used is not critical, provided a sufficient quantity is used to bind all free riboflavin in the sample.

The preferred method of the improved assay of the present invention will now be discussed in detail. The assay is a "homogeneous assay," which means that the end polarization readings are taken from a solution in which bound tracer is not separated from unbound tracer. This is a distinct advantage over heterogeneous immunoassay procedures such as those where the bound tracer must be separated from the unbound tracer before a reading can be taken.

The reagents for the fluorescence polarization assay of the present invention comprise antibody for phencyclidine and phencyclidine metabolites and tracer. Additionally, largely conventional solutions including a pretreatment solution, a dilution buffer, phencyclidine calibrators and phencyclidine controls are desirably prepared. Typical solutions of these reagents, some of which are described below, are commercially available in assay "kits" from Abbott Laboratories, Abbott Park, Ill.

All percentages expressed herein are weight/volume unless otherwise indicated. The tracer formulation presently preferred is 164 nanomolar tracer in: 0.1 molar tris buffer at pH 7.9; 10% sodium cholate; 0.1% sodium azide; and 0.01% bovine gamma-globulin. The antiserum formulation comprises rabbit serum diluted with: 0.1 molar sodium phosphate buffer at pH 7.5; 0.1% sodium azide; 0.01% bovine gamma-globulin; and 2% ethylene glycol (volume/volume). The dilution buffer comprises: 0.1 molar sodium phosphate at pH 7.5; 0.1% sodium azide; and 0.01% bovine gamma-globulin. The pretreatment solution comprises: 0.01% bovine gamma-globulin; 0.1 molar tris buffer at pH 7.5; 0.1% sodium azide; and 5 mg/ml riboflavin binding protein. Phencyclidine calibrators comprising phencyclidine in normal human urine at concentrations of 0.0, 25.0, 60.0, 120.0, 250.0 and 500.0 nanograms per milliliter, with 0.1% sodium azide as a preservative are useful. Phencyclidine controls comprising phencyclidine in normal human urine are provided at concentrations of 35.0 and 250.0 nanograms per milliliter with 0.1% sodium azide as a preservative are also useful.

The preferred procedure is especially designed to be used in conjunction with the Abbott TDx ® Analyzer available from Abbott Laboratories, Irving, Tex. Fifty microliters of urine is required. The calibrators, controls, or unknown samples are pipetted directly into the sample well of the TDx ® sample cartridge. One of the advantages of this procedure is that the sample does not require any special preparation. The assay procedure from this point is fully automated.

If a manual assay is being performed, then the sample is mixed with the pretreatment solution in dilution buffer and a background reading is taken. The tracer is then mixed with the assay. The antibody is then finally mixed into the test solution. After incubation, a fluorescence polarization reading is taken.

The fluorescence polarization value of each calibrator, control or sample is determined and is printed on the output tape of an instrument such as the Abbott TDx ® Analyzer. A standard curve is generated in the instrument by plotting the polarization of each calibrator versus its concentration using a nonlinear regression analysis. The concentration of each control or sample is read off the stored calibration curve and printed on the output tape.

With respect to the foregoing preferred procedure, it should be noted that the tracer, antibody, pretreatment solution, calibrators and controls should be stored between about 2° C. and about 8° C. while the dilution buffer should be stored at ambient temperature. A standard curve and controls should be run every two weeks, with each calibrator and control run in duplicate. All samples can be run in duplicate.

It should be understood that the foregoing detailed description and the following Examples are intended to be illustrative, but not limiting, with respect to the scope of the present invention. Various modifications will become apparent to one skilled in the art, and thus it is intended that the scope of the invention be defined solely by the claims and legal equivalents thereof.

EXAMPLES

Examples I through XVI describe experiments that were performed in accordance with the concepts of the present invention. Examples I through III are directed to preparation of an immunogen useful for producing antibody; Examples IV through IX and XI and XII are directed to the synthesis of precursors for immunogens and tracers; and Examples X and XIII through XVI are directed to the preparation of tracers.

EXAMPLE I 1-(1-Phenylcyclohexyl)piperazine Immunogen 1-(1-Phenylcyclohexyl)piperazine (25 mg) in 2 ml 50% methanol/water was added to bovine serum albumin (30 mg) in 2 ml distilled water with stirring. The pH was adjusted to 5.5 with 0.1N HCl. 1-Ethyl-3-(3-dimethylaminopropyl)carbodiimide (1 g) in 2 ml distilled water was added in four parts adjusting the pH with 0.1N HCl after each addition to about pH 5.5. The mixture was then stirred at room temperature for 18 hours. The mixture was dialysed in a cellulose dialysing tube (Spectra/Por ®, MW 12,000–14,000) against distilled water for four days. The solution from the dialysing tube was found to contain 2.7 mg/ml protein via the Biuret protein concentration determining method.

EXAMPLE II 4-(1-(1-Phenylcyclohexyl)) piperidinyl Chloroformate Immunogen 4-(1-(-Phenylcyclohexyl)) piperidinyl chloroformate (57 mg) in 0.25 ml dimethylformamide was added to bovine serum albumin (50 mg) in 2.5 ml 0.1M phosphate buffer pH 8.0 and stirred at room temperature for one hour. The mixture was dialysed in a cellulose dialysing tube (Spectra/Por ®, MW 12,000–14,000) against distilled water for 2 days and 0.90% saline for one day. The solution from the dialysing tube was found to contain 15.4 mg/ml protein via the Biuret protein concentration determining method.

EXAMPLE III

4-Amino-1-(1-phenylcyclohexyl) piperidine Immunogen

4-Amino-1-(1-phenylcyclohexyl) piperidine (40 mg) in 2.5 ml dimethylformamide and 7.5 ml distilled water was added to bovine serum albumin (69.5 mg) in 2.0 ml distilled water with stirring and the pH was adjusted to pH 5.0–5.5 with 0.1N HCl. 1-Ethyl-3-(3-dimethylaminopropyl)carbodiimide (60 mg) was added while maintaining the pH at 5.0–5.5 with 0.1N HCl. The mixture was stirred at room temperature for 2 hours. The mixture was dialysed in a cellulose dialysing tube (Spectra/Por ®, MW 12,000–14,000) against distilled water for 3 days. The solution from the dialysing tube was found to contain 4.19 mg/ml protein via the Biuret protein concentration determining method.

EXAMPLE IV

1-Benzyl-4-(1-cyanocyclohexyl) piperazine

1-Benzylpiperazine (Aldrich) (6.12 g) was dissolved in 10 ml deionized water and cooled to 0° C. Concentrated hydrochloric acid (3.6 ml) was added to adjust the pH to 5. After warming to room temperature, 3.6 ml cyclohexanone was added, followed by potassium cyanide (2.4 g) in 6 ml deionized water. The solution slowly became cloudy. After 18 hours, the solid was filtered. The solid was dissolved in chloroform, dried over Na$_2$SO$_4$, filtered and the solvent was removed in vacuo to yield pure 1-benzyl-4-(1-cyanocyclohexyl) piperazine.

EXAMPLE V

1-Benzyl-4-(1-phenylcyclohexyl) piperazine

To bromobenzene (0.6 g) and magnesium turnings (0.2 g) in 30 ml dry tetrahydrofuran under nitrogen was added a small crystal of iodine and 10 drops of 1,2-dibromoethane. After small bubbles began to form, the reaction was stirred and heated to reflux for 4 hours. After cooling to room temperature, 1-benzyl-4-(1-cyanocyclohexyl)piperazine (1 g) was added. After 23 hours, the reaction was filtered, 20 ml saturated aqueous ammonium chloride was added and the mixture was extracted with diethyl ether. The ether was dried and removed in vacuo. The residue was chromatographed on silica gel eluted with chloroform to yield pure 1-benzyl-4-(1-phenylcyclohexyl)piperazine.

EXAMPLE VI 1-(1-Phenylcyclohexyl)piperazine

1-Benzyl-4-(1-phenylcyclohexyl)piperazine (0.47 g) was dissolved in 86 ml methanol and 14 ml 0.2N HCl in methanol. The mixture was hydrogenated over palladium black (0.1175 g) and 3 atm. of hydrogen at room temperature for 1 hour. The reaction was filtered and the solvent was removed in vacuo. The residue was chromatographed on silica gel eluted with the appropriate mixture of methanol and chloroform to yield pure 1-(1-phenylcyclohexyl)piperazine.

EXAMPLE VII 1-(1-Cyanocyclohexyl)-4-hydroxyl piperidine

4-Hydroxypiperidine (Aldrich) (5 g) was dissolved in distilled water (14 ml), cooled to 0° C. and the pH was adjusted to between 4 and 5 by addition of concentrated hydrochloric acid and 4-hydroxypiperidine. After warming to room temperature, 5.2 ml cyclohexanone and 3.3 g potassium cyanide in water (9 ml) were added sequentially. After 18 hours stirring at room temperature, the solid was filtered. The solid was dissolved in 100 ml methylene chloride, dried over $Na_2SO_4$, filtered and the solvent was removed in vacuo to yield pure 1-(1-cyanocyclohexyl)-4-hydroxypiperidine.

EXAMPLE VIII 1-(1-Phenylcyclohexyl)-4-hydroxypiperidine

To bromobenzene (4.1 ml) and magnesium turnings (4 g) in 200 ml dry tetrahydrofuran under nitrogen was added a crystal of iodine and 10 drops of 1,2-dibromoethane. After small bubbles began to form, the reaction was stirred and heated to reflux for 4 hours. After cooling to room temperature 1-(1-cyanocyclohexyl)-4-hydroxypiperidine (2 g) was added. After 17 hours, the reaction was filtered, 120 ml saturated ammonium chloride was added and the mixture was extracted with ethyl ether. The ether layer was dried and the solvent was removed in vacuo. The residue was chromatographed on silica gel eluted with the appropriate mixture of methanol and chloroform to yield pure 1-(1-phenylcyclohexyl)-4-hydroxypiperidine.

EXAMPLE IX 4-(1-(1-Phenylcyclohexyl))piperidinyl Chloroformate 1-(1-Phenylcyclohexyl)-4-hydroxypiperidine (0.261 mg) was suspended in 5 ml dry benzene and 2 ml 10% phosgene in benzene was added. After stirring, stoppered for 3 hours at room temperature, 1 ml of chloroform was added. After 30 minutes, the solvent was removed in vacuo. Carbon tetrachloride (dry) (1 ml) was added and removed in vacuo to yield 4-(1-(1-phenylcyclohexyl))piperidinyl chloroformate as a white solid.

EXAMPLE X 4-(5-Fluoresceinylcarbamoyl)-1-(phenylcyclohexyl) piperidine 4-(1-(1-Phenylcyclohexyl))piperidinyl chloroformate (10 mg) and 5-aminofluorescein (10 mg) were dissolved in 2 ml dry pyridine and stirred at room temperature for about 18 hours. The reaction was chromatographed on silica gel preparative plates eluted with the appropriate ratio of methanol, chloroform and acetic acid to yield the desired tracer.

EXAMPLE XI 1-(1-Phenylcyclohexyl)-4-piperidone 1-(1-Phenylcyclohexyl)-4-hydroxypiperidine was dissolved in 15 ml glacial acetic acid and 0.3 ml concentrated sulfuric acid, and 1.9 ml Jones reagent (made from 26.72 g $H_2CrO_4$ and 23 ml $H_2SO_4$ diluted to 100 ml with water) was added dropwise. After stirring at room temperature for 20 minutes, 2 ml 2-propanol, Zn(Hg) (made from 1.5 g mossy zinc and 0.2 g mercuric chloride in 20 ml water and 0.25 ml concentrated hydrochloric acid at room temperature for 5 minutes), sodium citrate dihydrate (3.6 g) and 35 ml deionized water were added sequentially. After stirring the solution at room temperature for 30 minutes, the reaction was extracted with chloroform. The solvent was removed in vacuo. Distilled water was added and removed in vacuo. The residue was chromatographed on silica gel eluted with the appropriate mixture of methanol and chloroform to yield pure 1-(1-phenylcyclohexyl)-4-piperidone.

EXAMPLE XII

4-Amino-1-(1-phenylcyclohexyl)piperidine 1-(1-Phenylcyclohexyl)-4-piperidone (0.245 g) and ammonium acetate (1 g) were dissolved in 3.5 ml dry methanol. After stirring at room temperature for 10 minutes, sodium cyanoborohydride (0.1 g) was added and the reaction stoppered. After 20 hours, 0.1 ml concentrated hydrochloric acid was added followed by 10 ml water and the mixture was stirred for 1.5 hours. The solution was basified with potassium carbonate to pH 9 and extracted with methylene chloride. The methylene chloride was dried over $Na_2SO_4$ and removed in vacuo. The product distilled as a colorless, clear oil at 90°–130° C. in vacuo (about 5 mmHg).

EXAMPLE XIII 4-(4-Chloro-6-(5-fluoresceinylamino)-1,3,5-triazin-2-yl) amino-1-(1-phenylcyclohexyl)piperidine 4-Amino-1-(1-phenylcyclohexyl)piperidine (9 mg) and 5-((4,6-dichloro-1,3,5-triazin-2-yl)amino) fluorescein (17 mg) were dissolved in 1 ml methanol and 0.1 ml triethylamine. After stirring at room temperature for 30 hours, the solvent was removed in vacuo. The residue was chromatographed on silica gel preparative plates eluted with the appropriate mixture of methanol and chloroform to yield the tracer.

EXAMPLE XIV 4-(4-Chloro-6-(6-fluoresceinylamino)-1,3,5-triazin-2-yl) amino-1-(1-phenylcyclohexyl)piperidine The same procedure was used as in Example XIII except that 6-((4,6-dichloro-1,3,5-triazin-2-yl)amino) fluorescein was used instead of 5-((4,6-dichloro-1,3,5-triazin-2-yl)amino)fluorescein.

EXAMPLE XV 4-(Fluorescein-6-ylcarbonyl)amino-1-(1-phenylcyclohexyl) piperidine 6-Carboxyfluorescein (Calbiochem) (14 mg), N-hydroxysuccinimide (6 mg) and N,N'-dicyclohexylcarbodiimide (14 mg) were dissolved in 0.5 ml dry pyridine and stirred at room temperature, stoppered. After 1 hours, 4-amino-1-(1-phenylcyclohexyl) piperidine (9 mg) was added followed by 0.5 ml dry pyridine. After 15 hours, the reaction was chromatographed on silica gel preparative plates eluted with the appropriate mixture of methanol, chloroform and acetic acid.

EXAMPLE XVI 4-(Fluorescein-5-ylcarbonyl) amino-1-(1-phenylcyclohexyl)piperidine The same procedure was used as in Example XV except 5-carboxyfluorescein (Calbiochem) was used instead of 6-carboxyfluorescein.

We claim:

1. A compound having fluorescent properties and corresponding to the formula:

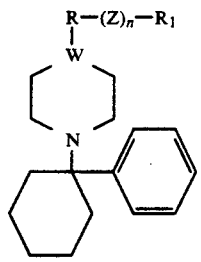

wherein

W is —CH— or —N—;

R is a linking group having a combined total, exclusive of hydrogen atoms, of from zero to eight carbon atoms and atoms selected from the group consisting of Cl, O, N, S, F, Br and I, of which total the number of atoms from said group is from zero to four, said linking group being a divalent straight or branched chain;

Z is —NH—, —CO— or

n is 1 when W is —CH—, and 0 or 1 when W is —N—; and

F1 is fluorescein bonded to Z at the 5- or 6-position of F1, or at any other position of F1 wherein F1 has the ability to retain its fluorescent properties.

2. The tracer according to claim 1 wherein R-Z is selected from —NH—CO—, —CO—NH—, —CNH—NH—, —NH—CO—NH—, —NH—CS—NH—, —O—CO—NH—, and —O—CS—NH—.

3. The compound according to claim 2 wherein the compound is 4-(5-fluoresceinylcarbamoyl)-1-(1-phenylcyclohexyl)-piperidine.

4. The compound according to claim 2 wherein the compound is 4-(6-fluoresceinylcarbonyl)amino-1-(1-phenylcyclohexyl)piperidine.

5. The compound according to claim 2 wherein the compound is 4-(5-fluoresceinylcarbonyl)amino-1-(1-phenylcyclohexyl)piperidine.

* * * * *